United States Patent [19]

Jou et al.

[11] Patent Number: 5,210,040
[45] Date of Patent: May 11, 1993

[54] PROCESS FOR COUPLING ANTIBODIES OR ANTIBODY FRAGMENTS TO LIPOSOMES

[75] Inventors: Yi-Her Jou, Vernon Hills; Roger C. Hu, Libertyville; Peter A. Lagocki, Park Ridge, all of Ill.

[73] Assignee: Abbott Laboratories, Abbott Park, Ill.

[21] Appl. No.: 485,395

[22] Filed: Feb. 22, 1990

Related U.S. Application Data

[60] Division of Ser. No. 312,430, Feb. 17, 1989, Pat. No. 4,971,916, which is a continuation of Ser. No. 85,918, Jul. 29, 1987, abandoned.

[51] Int. Cl.$^5$ ................ G01N 33/544; G01N 33/563
[52] U.S. Cl. .................................. 436/528; 424/450; 436/512; 436/829
[58] Field of Search ............... 436/829, 512, 528, 532, 436/533; 530/387; 264/4; 424/450

[56] References Cited

U.S. PATENT DOCUMENTS

| | | | |
|---|---|---|---|
| 4,429,008 | 1/1984 | Martin et al. | 428/402.2 |
| 4,598,051 | 7/1986 | Papahadjopoulos et al. | 436/512 |
| 5,008,109 | 4/1991 | Tin et al. | 424/422 |
| 5,078,998 | 1/1992 | Bevan et al. | 424/85.8 |

OTHER PUBLICATIONS

Federation Proceedings, vol. 43, 1984, p. 1971, abstract No. 3218, Washington, U.S.; Y-H. You et al.: "Use of Heterobifunctional Cross-Linking Reagents to Prepare Antibody-Liposome Aggregation During Conjugation During Conjugation".

Chemistry and Physics of Lipids, vol. 40, 1983, pp. 347-350, Amsterdam, NL; T. D. Heath et al.: "The Development and Application of Protein-Liposome Conjugation Techniques".

*Primary Examiner*—Esther L. Kepplinger
*Assistant Examiner*—Nancy Parsons
*Attorney, Agent, or Firm*—Lawrence S. Pope; Thomas M. Breininger

[57] ABSTRACT

The present invention provides for novel homogeneous immunoassay systems involving complement-mediated lysis of marker-encapsulating lipid vesicles (liposomes) for detection of analyte in a fluid sample. These systems do not require the separation of unbound antigens and/or antibody conjugates yet provide highly sensitive procedures for analyte detection. Liposomes containing a marker, are coupled to antibody fragments in a way which confers the liposomes with immunological specificity yet avoids sensitizing the liposomes to complement mediated lysis in the absence of analyte. Antibody sensitized liposomes (the first reagent) are sequentially incubated with an analyte-containing sample, and optionally "dummy" liposomes, which do not contain encapsulated marker, a second antibody (the second reagent), and finally with a complement source such as plasma. Complement is activated by the liposome-antibody-antigen-second antibody complex causing liposome lysis and a concomitant release of marker. Also provided are methods for preparing antibody sensitized liposomes in the presence of a polysaccharide capable of forming a reversible gel and methods for preparing derivatized Fab' antibody fragments for coupling to lipid vesicles.

4 Claims, No Drawings

PROCESS FOR COUPLING ANTIBODIES OR ANTIBODY FRAGMENTS TO LIPOSOMES

This is a division of application Ser. No. 312,430, filed Feb. 17, 1989, now U.S. Pat. No. 4,971,916, which is a continuation application of prior application Ser. No. 085,918, filed on Jul. 29, 1987, which is now abandoned.

BACKGROUND OF THE INVENTION

The present invention pertains to homogeneous immunoassay systems involving complement-mediated lysis of liposomes containing markers.

Liposomes are micron-sized spherical shells of amphipatic molecules which isolate an interior aqueous space from the bulk exterior aqueous environment. They can be made to contain hydrophobic molecules within their membrane, or hydrophilic markers within their internal aqueous space, or both. Because of this versatility, liposomes are of interest both as potential vehicles for the delivery of drugs in vivo and as the basis for immunoassay systems in vitro.

Various formats for liposome immunoassay systems have been developed including heterogeneous and homogeneous systems. Heterogeneous systems, which typically require an initial separation of bound and unbound forms of tracer, are described in O'Connell, et al., *Clin. Chem.*, 31:1424-1426 (1985) and MacCrindle, et al., *Clin. Chem.*, 31:1487-1490 (1985). Homogeneous methods, such as those based on i) complement-mediated lysis, ii) melittin-mediated lysis, iii) color changes induced by cation-responsive dyes in perturbed membranes, and iv) enhanced agglutination, have also been described. Some of these methods rely on liposomes to generally amplify immunological reactions whereas others rely on the utility of liposomes to encapsulate marker substances within the liposome and to subsequently release them in proportion to the amount of analyte present in a sample.

An immunoassay system of particular interest to the background of the invention is the Liposome Immuno-Lytic Assay (LILA) which involves the antibody-triggered complement-mediated lysis of liposomes. In an exemplary assay format, a liposome encapsulating a marker is first made immunoreactive by association of a first immunological binding pair member (e.g., an antigen) with its surface. The liposome is then incubated with a fluid sample to be analyzed for the presence of the corresponding binding pair member (e.g., an antibody). Typically, the binding of antibody to antigen (pre-bound to the liposome surface) generates a liposome immune complex and, upon the addition of serum, complement activation is initiated leading to lysis of the liposome and release of the internal marker substance. The amount of analyte present in the sample is proportional to the amount of marker substance released.

Liposome lysis can be detected in a variety of ways and depends upon the nature of the marker initially encapsulated within the liposome. Kataoka, et al., *Eur. J. Biochem.*, 24:123 (1971), for example, describe Lipid A sensitized liposomes which release a spectrophotometrically detectable glucose marker when incubated with an anti-Lipid A anti-serum and complement source. Yet another means for detecting lysis involves initially encapsulating within the liposome a fluorophore at self-quenching concentrations. Upon liposome lysis, an extreme dilution of the fluorophore occurs and this dilution re-establishes fluorescence. The increase in fluorescence is proportional to the amount of analyte present in the sample. Ishimori, et al., *J. Immuno. Methods*, 75:351-360 (1984) describe an immunoassay technique using immunolysis of liposomes to measure antibody against protein antigens such as human IgG. The marker used was carboxyfluorescein and the technique was reported to be effective at detecting $10^{-15}$ mole of anti-human IgG antibody or human IgG. Similarly, Yasuda et al., *J. Immun. Methods*, 44:153-158 (1981), describe the utilization of complement-mediated immune lysis of liposomes entrapping carboxyfluorescein at self-quenching concentrations to measure anti-glycolipid antibody.

The use of antibody sensitized liposomes in Liposome Immuno-Lytic Assays presents a number of system design problems not present in assays employing antigen coupled liposomes. Of interest to the background of the present invention are references describing developments in the art relating to procedures for coupling antibodies to liposome surfaces (Heath, T.D. and Martin, F.J., *Chemistry & Physics of Lipids*, 40:347-358 (1986); Martin, F.J. and Kung, V.T., *Annals New York Academy of Sciences*, 446:443-456 (1985)) which describe binding characteristics of antibody-bearing liposomes; and especially those references which relate to avoidance of liposome aggregation—a phenomenon which can seriously limit the sensitivity of LILA's. As one example, Jou, et al., *Fed. Proc., Fed. Am. Soc. E. Biol.*, 43:1971 (1984) disclose coupling procedures designed for avoidance of aggregation of antibody-sensitized liposomes through a series of steps including: (1) limiting the average number of reactive functional groups per antibody molecule to less than one; (2) providing for early "quenching" during the coupling reaction; and, (3) employing dialysis to remove uncoupled antibodies. In this reference however, only liposome aggregation as a result of antibody-liposome coupling was addressed and no information was provided regarding the use of antibody-coupled liposomes for immunoassays.

Umeda, et al., *J. Immun. Meth.*, 95:15-21 (1986) (and Umeda, et al., Jap. Patent Appln. No. Sho 59 [1984-261806]) describe a series of studies regarding a complement-mediated liposome immune lysis assay using carboxyfluorescein-entrapped liposomes sensitized with antibody to C-reactive protein (CRP) antigen. Whole antibodies, derived from different animal sources, were modified and coupled to liposomes utilizing a heterobifunctional cross-linking reagent, N-succinimidyl-3-(2 pyridyldithio)-propionate (SPDP) and dithiothreitol (DTT), a reducing agent. However, upon coupling certain antibodies, e.g., rabbit antibodies, to dithiopyridyl-substituted dipalmitoylphosphatidylethanolamine (DTP-DPPE) liposomes, complement activation and liposome lysis occurred even in the absence of sample containing analyte. The low level of complement reagent required to minimize this non-specific lysis necessarily lowered the overall sensitivity of the assay. In addition, only certain animal sources of complement, i.e., guinea pig serum, proved to be effective reagents and this effectiveness also depended upon the animal source of the antibody coupled to the liposome. For example, goat antibody was suitable as the antibody bound to the liposome, but was not suitable as the secondary antibody. Although the assay sensitivity was in proportion to the amount of antibody bound to the liposome, when more than 400 $\mu$g of IgG/$\mu$mol of lipid was bound to the liposomes, liposomes became fragile and their spontaneous release of carboxyfluorescein increased irrespective of the liposome lipid composition. The sensitivity of the assay was improved by purification of whole antibody (by passage through an affinity chromatography column) prior to binding to liposomes. However, sensitivity was not increased when Fab' antibody fragments (which were expected to be coupled to liposomes more efficiently than IgG) were bound to liposomes. The Fab' antibody fragments of the reference were prepared by reducing F(ab')$_2$ antibody fragments with mercaptoethylamine and were then coupled via thiol residues to derivatized liposomes containing DTP-DPPE. In the attempt to explain the lack of improved sensitivity over that obtained using liposomes bearing whole goat antibody, it was speculated that the affinity of Fab' antibody fragments for antigen may be reduced during the drastic pepsin digestion at pH 4.5. It was thus suggested that the use of "high affinity" Fab' fragments would result in a much higher sensitivity than use of whole IgG.

The coupling of Fab' antibody fragments to liposomes via a disulfide exchange reaction requires either a sulfhydryl reactive derivative on the liposome or a derivatization of the sulfhydryl group on the Fab'antibody fragment. For example, Martin, et al., *Biochemistry*, 20:4229 (1981), describes the use of N-[3-2-pyridyldithio)propionyl]phosphatidylethanolamine (PDP-PE) liposomes, in a disulfide exchange reaction. The sulfhydryl reactive derivative is a pyridyldithio derivative. Martin, et al., *J. Biol. Chem.* 257:286 (1982), describes the use of N-[4-(p-maleimidophenyl)-butryl]phosphatidylethanolamine (MPB-PE) liposomes having reactive maleimide moieties for forming an essentially irreversible antibody-vesicle linkage which did not involve the usual disulfide linkage but rather involved the more stable thioether linkage. The liposomes of the two Martin references did not contain an encapsulated fluorophore as these liposomes were intended for "targetting" use rather than for use in an immunoassay. Bredehorst, et al., *Biochemistry*, 25:5693-5698 (1986) describes the coupling of Fab' fragments to MPB-PE liposomes. These liposomes did contain encapsulated fluorophore but the liposomes were noted to release up to 95% of the entrapped fluorophore. To overcome this leakage problem, a decrease in the molar concentration of the MPB-PE anchor in the liposomes was required which caused a corresponding decrease in the number of Fab' molecules bound per liposome. No evidence was given as to whether such coupled liposomes would be functional in an immunoassay.

A number of references have described derivatization of Fab' antibody fragments for use in the preparation of bispecific antibodies—hybrid immunoglobulins provided with two different antigen-binding sites through a chemical re-association of monovalent fragments derived. See, e.g., Brennan, et al., *Science*, 229:81 (1985) and Paulus, H.P., PCT Patent Application WO 85/04811. Both references show the preparation of Fab' thionitrobenzoate derivatives in which arsenite is used as a complexing agent to stabilize vicinal dithiols and to impede intramolecular disulfide formation.

In sum, several immunoassay systems involving complement mediated lysis of marker-encapsulating, antibody bound liposomes have been described. However, none of these are homogeneous systems totally responsive to the need in the art for highly sensitive assays for antigens in fluid samples.

BRIEF SUMMARY OF THE INVENTION

The present invention provides for novel homogeneous immunoassay systems involving complement-mediated lysis of marker-encapsulating lipid vesicles (liposomes) for detection of analyte in a fluid sample. These systems do not require the separation of unbound antigens and/or antibody conjugates yet provide highly sensitive procedures for analyte detection.

Liposomes containing a marker, e.g., a fluorescent marker, are coupled to antibody fragments (variously referred to as liposome-antibody conjugates or antibody sensitized liposomes). The antibody fragments of the invention confer the liposomes with immunological specificity yet avoid sensitizing the liposomes to complement mediated lysis in the absence of analyte. Antibody sensitized liposomes (the first reagent) are sequentially incubated with an analyte-containing sample, a second antibody (the second reagent), and finally with a complement source such as plasma. Complement is activated by the liposome-antibody-antigen-second antibody complex, and causes liposome lysis, a concomitant release of fluorophore and an increase in observable fluorescence.

Antibody of the first reagent may be an anti-analyte F(ab')$_2$ antibody fragment, or an anti-analyte Fab' antibody fragment. Antibody of the second regent may be provided in either soluble form, or in insoluble form e.g., bound onto carboxylated polystyrene particles or coupled to a third antibody in the form of a "double antibody" immune precipitate. Where the antibody of the second reagent is provided in an insoluble form, the analyte-containing sample is preferably incubated with the second reagent, to form an analyte-second antibody complex, prior to incubation with the first reagent. Where the second reagent consists of soluble antibodies, the first reagent is incubated with the analyte containing sample prior to incubation with the second reagent.

In a presently preferred system, designed for detection of human chorionic gonadotropin (HCG) in a fluid sample, liposomes containing a fluorophore marker, such as calcein, are coupled to Fab' antibody fragments, e.g., goat anti-HCG Fab' antibody fragments, and incubated with an HCG-containing sample in the presence of dummy liposomes. This is followed by incubation with a second soluble antibody, e.g., goat anti-HCG IgG, and finally with complement, e.g., goat serum, leading to liposome lysis and an increase in observable fluorescence.

In another presently preferred system liposomes containing a fluorescent marker, e.g., calcein, are coupled to F(ab')$_2$ antibody fragments, e.g., goat anti-HCG F(ab')$_2$ antibody fragments, and the antibody sensitized liposomes are sequentially incubated with an HCG-containing sample and then with a second antibody, e.g., goat anti-HCG antibody, in solution form to form liposome-antibody-HCG-second antibody complexes, which are then lysed with complement, e.g., either human plasma or rabbit serum. In another preferred system, the second antibody, e.g., goat anti-HCG-antibody, is coated onto carboxylated polystyrene particles or coupled to a third antibody, e.g., rabbit anti-goat IgG antibody, as a double antibody precipitate.

In another aspect of the invention designed to obtain improved sensitivity of the liposome immunolytic assay, antibody sensitized liposomes are mixed with "dummy" lipid vesicles, liposomes which do not contain encapsulated marker, prior to incubation with the analyte containing sample and with a second antibody.

In another of its aspects, the present invention provides methods for preparing antibody sensitized liposomes in a manner which minimizes liposome aggregation both during preparation and storage. In a preferred method for reducing lipid vesicle aggregation during antibody lipid vesicle conjugation, lipid vesicles having thiol groups are conjugated with modified antibody, i.e., Fab' and F(ab')$_2$ antibody fragments with thiol-reactive groups, in the presence of a polysaccharide capable of forming a reversible gel. The gel reaction mixture is cooled to form a gelate, unreacted thiol groups on the liposomes are alkylated, and the gelate, containing liposome-antibody conjugates, is washed and may be placed in a buffer for storage. By minimizing liposome aggregation, the accessible surface area of each liposome is increased as is the total reactivity of liposome preparations, thereby enhancing the efficacy of their diagnostic and therapeutic applications.

In another of its aspects, the present invention provides methods for preparing Fab' antibody fragments whereby antibody affinity for its complementary antigen is retained resulting in antibody sensitized liposomes with greatly improved sensitivity in a LILA. According to another aspect of the invention, antibody fragments are chemically modified to bear functional group(s) which are reactive toward certain moieties on the liposome surface and therefore are able to form antibody-liposome covalent linkages upon their mixing with liposomes. Illustratively, F(ab')$_2$ antibody fragments, prepared from whole antibody, e.g., goat anti-HCG antibody, are treated with a dithiol complexing agent, such as sodium arsenite, to stabilize vicinal dithiols and impede intramolecular disulfide formation, in the presence of a reductive cleavage agent such as cysteine-HCl. The resulting Fab' antibody fragments are then treated with a thiol activating agent, such as 5,5'-dithiobis(2-nitrobenzoic acid), to form thionitrobenzoate derivatized Fab'antibody fragments (TNB-Fab'). These derivatized Fab'antibody fragments may then be coupled to lipid vesicles to form antibody sensitized liposomes.

Other aspects and advantages of the present invention will be apparent upon consideration of the following detailed description thereof which includes numerous illustrative examples of practice of the invention.

DETAILED DESCRIPTION

The following illustrative, Example 1, relates to the preparation of thiol-containing multi-lamellar vesicles (MLV). Example 2 relates to the preparation of anti-HCG F(ab')$_2$ fragments and to the coupling of anti-HCG F(ab')$_2$ fragments to liposomes in agarose gels. Example 3 relates to methods for preparation of anti-HCG Fab' fragments, specifically the thionitrobenzoate derivative of Fab' (TNB-Fab') and to the coupling of these derivatized fragments to liposomes in agarose gels.

Illustrative examples 4 and 5 relate, respectively to the preparation of double antibody immune precipitates and to the coating of carboxylated polystyrene with antibodies.

Example 6 relates to an immunoassay for the quantitative analysis of the amount of HCG in a sample using anti-HCG Fab'-coupled liposomes as the first reagent, a soluble antibody as the second reagent, and dummy liposomes.

Example 7 relates to an HCG immunoassay using anti-HCG F(ab')$_2$-coupled liposomes as the first reagent and soluble antibodies as the second reagent. Example 8 relates to an HCG immunoassay using anti-HCG F(ab')$_2$-coupled liposomes as the first reagent and a double antibody immune precipitate as the second reagent. Example 9 relates to an HCG immunoassay using anti-HCG F(ab')$_2$-coupled liposomes as the first reagent and antibody coated carboxylated polystyrene particles as the second reagent.

The examples which follow are for illustrative purposes and are not intended in any way to limit the scope of the invention.

EXAMPLE 1

Preparation of Thiol-Containing Multilamellar Vesicles (HS-MLV)

A mixture of 20 μmole sphingomyelin, 20 μmole cholesterol, 2 μmole dimyristoylphosphatidyl-thioglycerol (DMPTG) and a trace amount of $^{14}$C-sphingomyelin in 0.64 ml chloroform-methanol (9:1) is rotovaporated to dryness in a 5 ml pear-shape flask. The flask containing the lipid film is kept in vacuo and dessicated overnight. Three ml of 100 mM calcein and 1 g of 50–100 μm glass beads are added to the flask and the mixture is vortexed for 15 minutes at 1200 rpm. After the addition of 10 ml HEPES buffer (50 mM HEPES, 50 mM sucrose, 150 mM NaCl, pH 7.5), the mixture is left to stand until the glass beads settle to the bottom of flask. The supernatant is removed, combined with an additional portion (20 ml) of HEPES buffer, and centrifuged at 41,000×g for 30 minutes at 4° C. The pellet of liposomes is resuspended in 1 ml of HEPES buffer. Unless otherwise indicated, this liposome preparation is used for the subsequent examples.

EXAMPLE 2

A. Preparation of Anti-HCG F(ab')$_2$ Fragments

Anti-HCG F(ab')$_2$ fragments are prepared according to the method of Nisonoff, et al., *Arch. Biochem. Biophy.*, 89:230–244 (1960) from affinity purified goat anti-HCG antibodies. Typically, a portion of affinity purified antibody solution in phosphate-buffered saline, pH 7.2 (PBS) is acidified to pH 4 by adding acetic acid. The preferred concentration of antibodies at this point is 1 mg/ml. Pepsin is added to reach a final concentration of 20 μg/ml. The mixture is incubated at 37° C. overnight. The reaction is stopped by adding 6N NaOH to bring the pH of the reaction mixture to pH 7.5. The concentration of the digested antibody fragments solution is concentrated to 20 mg/ml. The F(ab')$_2$ fragments are purified by gel-filtration high performance liquid chromatography using a Spherogel TSK-3000SWG column (2.15 cm×30 cm), with a Spherogel TSK-G guard column (2.15 cm×7.5 cm). (Beckman Instruments, Inc., Fullerton, Calif. 92634).

EXAMPLE 2

B. Coupling of Anti-HCG F(ab')$_2$ Fragments to HS-MLV in Agarose Gel

To 1 ml of goat F(ab')$_2$ (anti-human chorionic gonadotropin), 10 mg/ml, containing trace $^{125}$I-F(ab')$_2$ in HEPES buffer, is added with stirring 40 μl of a 30 mM succinimidyl 4-(N-maleimidomethyl)-cyclohexan-1-carboxylate (SMCC) in N,N-dimethylformamide. The resulting reaction mixture is stirred for 1 hour at room temperature and then chromatographed on a PD-10 (Phamacia, Inc., Piscataway, N.J.) column preequilibrated with HEPES buffer. A 0.5 ml portion of the pooled fractions of modified F(ab')$_2$ (1 mg/ml) is mixed with 0.25 ml freshly prepared 3.5% Seaprep agarose (FMC, Marine Colloids Division, Rockland, Me. 04841) or any other gel capable of forming a reversible gel, such as, Agar-agar, Agar(Noble), or gelatin, and 0.5 ml of HS-MLV (1 μmole/ml) liposomes, prepared according to Example 1.

The resulting reaction mixture is transferred to a 1 ml glass pipette and cooled at 4° C. for 15 minutes to gelate. The gelated reaction mixture is left to stand at room temperature overnight. The gel is removed from the pipette and placed into 100 ml HEPES buffer containing 10 mM iodoacetamide. After shaking for 2 hours at 4° C. the washing buffer is removed and a fresh 100 ml portion of buffer is charged to wash the gel at 4° C. overnight. The liposomes can be stored in such a gel matrix until they are to be used. After the washing procedure is repeated at least two times, a segment (ca. 0.025 ml) of the gel is placed into 0.15 ml of HEPES-gelatin buffer, (50 mM HEPES, 50 mM sucrose, 150 mM NaCl, pH 7.5 plus 1 mg/ml gelatin) fragmented by pipetting, transferred into 1.25 ml of pre-warmed (37° C.) HEPES-gelatin buffer, and is mixed by repeated pipetting in a 37° C. water bath until the gel melts.

The amount of protein coupling to liposomes, as determined by $^{125}$I-labelled F(ab')$_2$ and $^{14}$C-sphingomyelin tracer in the preparation, is typically in the range of 20–80 μg of F(ab')$_2$ coupled to each μmole of liposomes. The amount of F(ab')$_2$ coupling per liposome is directly proportional to the input concentration of modified F(ab')$_2$.

EXAMPLE 3

A. Preparation of Anti-HCG Fab' Fragments

Anti-HCG Fab' fragments are prepared and derivatized into a thiol-reactive form according to a modification of the methods of Parham, et al., *J. Immunol. Method*, 53:133–173 (1982) and Brennan, et al., *Science*, 229:81–83 (1985). To 1.28 ml of goat F(ab')$_2$ (anti-human chorionic gonadotropin), 16 mg/ml, containing trace $^{125}$I-F(ab')$_2$, in PBS, is added with stirring 158 μl of 0.1 M NaAsO$_2$ containing 20 mM EDTA. The reductive cleavage reaction is started by adding 158 μl of 0.1 M cysteine-HCl. The reaction mixture is overlayed with nitrogen and is incubated with stirring at 37° C. for one hour. The reaction is quenched by adding 19 mg of 5,5'-dithiobis-(2-nitrobenzoic acid). After stirring overnight, at room temperature, the mixture is chromatographed on a PD-10 column (Pharmacia, Piscataway, N.J.) pre-equilibrated with PBS, and then on a size exclusion high performance liquid chromatography column; Spherogel TSK-2000SWG (2.15 cm × 30 cm) with a Spherogel TSK-G guard column (2.15 cm × 7.5 cm) (Beckman Instrument, Inc., Fullerton, Calif. 92634). The purified thionitrobenzoate derivative of Fab' (TNB-Fab') is concentrated to 6 mg/ml using an ultrafiltration unit CX-10 (Millipore Corp. Bedford, Mass. 01730).

B. Coupling of Anti-HCG Fab' Fragments to HS-MLV in Agarose Gel

A 2 ml portion of TNB-Fab' (0.05 to 1 mg/ml) is mixed with 0.5 ml freshly prepared HS-MLV (5 μmole/ml), prepared according to Example 1, in a 12 mm × 75 mm test tube. The empty space in the top portion of the tube is briefly flushed with a stream of nitrogen before the tube is capped. The reaction mixture is then mixed on a circular rotator at ca. 50 rpm at room temperature for a period of 4 hours to overnight. To the reaction mixture is then added 0.28 ml of 0.1 M iodoacetamide and 0.35 ml of 3.5% Seaprep Agarose. The resulting mixture is then transferred to a 1 ml glass pipette and cooled at 4° C. for 15 minutes to gelate. The gelated mixture is left to stand at room temperature for 1 hour. The gel is removed from the pipette, washed, and then stored in the HEPES buffer in the same manner as that described in Example 2B. To isolate liposomes for, e.g., use in an assay, the liposome-containing gel is melted and diluted in HEPES-gelatin buffer according to the method described in Example 2B.

The level of protein coupling to liposomes, as determined by $^{125}$I-labelled Fab' and $^{14}$C-sphingomyelin tracer, is typically in the range of 10 to 700 μg of Fab' coupled per μmole of liposomes. While a direct comparison cannot be made, due to differences in the lipid compositions of the liposomes, the coupling chemistries and the antibody forms used, i.e., whole antibody versus antibody fragments, this example illustrates that Fab'-liposomes prepared by this method, at a coupling level of Fab'/lipid as high as 700 μg/μmole, are stable for at least four months in contrast to previous methods, i.e., Umeda, et al., which demonstrated that coupling at a level of 160 μg/μmole lipid was more stable than coupling at 400 μg IgG/μmole of lipid.

EXAMPLE 4

Preparation of Double Antibody Immune Precipitates

A solution of affinity purified goat anti-HCG (10 mg/ml) is made in 0.1 M phosphate buffer, pH 7.2. A 0.7 ml (3 mg/ml) IgG preparation of rabbit anti-goat IgG Fc fragment is added, and the resulting mixture is incubated at 37° C. for 1 hour. To the mixture is added 2.7 ml (1.6 mg/ml) of rabbit anti-goat IgG antiserum and the incubation is continued at 37° C. for 2.5 hours and then at 4° C. for 3 days. The mixture is centrifuged at 1000 × g for 15 minutes. The supernatant is removed and the precipitate is resuspended in 5 ml phosphate buffer. The centrifugation resuspension process is repeated once. The precipitate, containing double antibody immune precipitates, is finally suspended in 1 ml of HEPES-gelatin buffer.

EXAMPLE 5

Coating of Carboxylated Polystyrene with Antibodies

A 4 ml suspension containing 0.48% (w/v) carboxyl-polystyrene particles (0.8 μm diameter) and 0.2 mg/ml of affinity purified goat anti-HCG antibodies is made and mixed at room temperature on a rotating mixer for 2 hours. The suspension is centrifuged at 3000 × g for 10 min. and the pelleted particles are resuspended in 5 ml of phosphate buffer. The centrifugation resuspension process is repeated once, and the particles are finally resuspended in 5 ml of HEPES-gelatin buffer.

EXAMPLE 6

Immunoassay Using Anti-HCG Fab' Coupled Liposomes and a Second Antibody in Soluble Form and Dummy Liposomes as Non-specific Reaction Inhibitors

A. Non-Specific Lysis of Fab'-Liposomes

Non-specific, i.e., analyte independent, lysis of Fab'-liposomes is demonstrated using goat serum as the complement reagent. To a series of duplicate tubes is added 150 μl of Fab'-liposomes (1.3 μM), prepared according to Example 3B, and 150 μl of goat serum at various concentrations ranging from 5% to 40%. The resulting mixture is incubated at 37° C. for 12 minutes. At the end of this period, the reaction is stopped by adding 700 μl of HEPES-gelatin buffer containing 35.7 mM EDTA. The extent of liposome lysis is determined by measuring the fluorescent signal in each tube. The results are summarized in Table 1.

TABLE 1

| Goat Serum (%) | Non-specific Liposome Lysis (%) |
|---|---|
| 40 | 63 |
| 20 | 53 |
| 10 | 4 |
| 5 | 0.4 |

The extent of non-specific lysis of liposomes coupled with whole antibody, or with F(ab')$_2$ antibody fragments is much higher than obtained using Fab'antibody fragments. For example, where whole antibody (32–281 μg/ml liposomes) is coupled to liposomes and only extremely low levels of human plasma are used, i.e., 0–2.5%, non-specific lysis levels of from approximately 10% to 60% are observed and if 1.25% to 2.5% human plasma is used, 20–60% non-specific liposome lysis is obtained.

B. Preparation of Dummy Liposomes for Inhibition of Non-Specific Lysis i) Lipid Film A mixture of 10 μmole sphingomyelin, 10 μmole cholesterol, 1 μmole DMPTG and a trace amount of 14$_C$-sphingomyelin in 0.32 ml chloroform-methanol (9:1) is roto-vaporated to dryness in a 5 ml pear-shape flask. The flask containing the lipid film is kept dessicated and in vacuo until it is used.

ii) Multi-lamellar Vesicles (MLV)

Three ml of HEPES buffer and 1 g of 50–100 μm glass beads are added to the flask containing the dried lipid film and the mixture is vortexed for 15 minutes at 1200 rpm. After the addition of 10 ml HEPES buffer containing 10 mM iodoacetamide, the mixture is left to stand until the glass beads settle to the bottom of the flask. The supernatant is removed, combined with an additional portion (20 ml) of HEPES buffer containing 10 mM iodoacetamide, and incubated for 1 hour at room temperature. The liposomes are isolated by the same centrifugation and resuspension process as those described in Example 1.

iii) Sonicated Unilamellar Vesicles (SUV)

To a dried lipid film is added 20 ml of HEPES buffer. The resulting mixture is then sonicated in a special ultrasonic cleaner (G112SP1, Laboratory Supply Company, Inc., Hicksville, N.Y. 11081) for 2.5 hours at a bath temperature of 50° C. After the addition of 37 mg of iodoacetamide, the vesicle suspension is stirred at room temperature for 1 hour. At the end of this period the vesicle suspension is chromatographed on a Sephadex ™ G-25 column (1.5 cm×28 cm) pre-equilibrated with HEPES buffer.

C. Inhibition of Non-specific Lysis by Dummy Liposomes

To a series of duplicate tubes is added 150 μl of 1.3 μM Fab'-liposomes, prepared according to Example 3B, containing various concentrations of dummy liposomes and 150 μl of 15% goat serum. A 15% concentration of goat serum was used in order to more readily observe any inhibitory effects of dummy liposomes. The resulting mixture is incubated at 37° C. for 12 minutes. At the end of this period, the reaction is stopped by adding 700 μl HEPES-gelatin buffer containing 35.7 mM EDTA. The extent of liposome lysis is determined by measuring the fluorescent signal in each tube. The results are summarized in Table 2.

TABLE 2

| Dummy Liposome Concentration (μM) | % Fab'-liposome Lysis |
|---|---|
| 0 | 40 |
| 1.3 | 38 |
| 2.5 | 33 |
| 5.0 | 27 |
| 10.0 | 18 |
| 20.0 | 10 |
| 40.0 | 6 |

D. Immunoassay for HCG Using Anti-HCG Fab'Coupled Liposomes and a Second Antibody in Soluble Form in the Presence of an Excess Concentration of Dummy Liposomes To each of a set of duplicate tubes is added 25 μl of a liposome suspension containing 8 μM Fab'-liposomes, prepared according to Example 3B, and an excess concentration of dummy liposomes (1.6 mM). To each set of duplicate tubes is added 25 μl of a standard HCG solution (2, 1, 0.5, 0.25, 0.1, 0.05 and 0 mIU/ml). The resulting mixture is incubated at 37° C. for 30 minutes. To each tube is then added 25 μl of goat anti-HCG IgG (3 mg/ml) and the resulting mixture is incubated at 37° C. for 5 minutes. The lysis of liposomes is initiated by the addition of 75 μl of a freshly prepared complement reagent (100% goat serum-used in excess to obtain a maximum reaction rate) followed by incubation at 37° C. for 5 minutes. At the end of this period the reaction is stopped by adding 700 μl of HEPES-gelatin buffer containing 35.7 mM EDTA. The extent of liposome lysis is determined by measuring the fluorescent signal in each tube. The results are summarized in Table 3.

TABLE 3

| HCG (mIU/ml) | % Fab'-liposome Lysis Fab' coupled/liposome (μg/μmole) | | |
|---|---|---|---|
| | 10 | 123 | 722 |
| 0.05 | 0 | 0 | 1 |
| 0.10 | 0 | 2 | 2 |
| 0.25 | 3 | 3 | 6 |
| 0.50 | 4 | 7 | 20 |
| 1.00 | 12 | 15 | 31 |
| 2.00 | 25 | 32 | 49 |

EXAMPLE 7

Immunoassay Using Anti-HCG F(ab')$_2$ Coupled Liposomes and a Second Antibody in Soluble Form To each of a set of ten tubes is added 50 μl of a 4 μM anti-HCG F(ab')$_2$ coupled liposome suspension prepared according to Example 2B. To each set of duplicate tubes is added 50 μl of a standard HCG solution (780, 300, 10, 2 and 0 mIU/ml). The resulting mixture is incubated at 37° C. for 30 minutes. To each tube is then added 50 μl of affinity purified goat anti-HCG antibodies (0.35 mg/ml), and the resulting mixture is allowed to incubate at 37° C. for 30 minutes. The lysis of liposomes is initiated by the addition of 150 μl of a freshly prepared complement reagent (60% human plasma or rabbit serum) followed by incubating the mixture at 37° C. for 2 minutes. At the end of this period, the reaction is stopped by adding 700 μl of HEPES-gelatin buffer containing 35.7 mM EDTA. The difference between the fluorescent signal of tubes receiving HCG solution and the signal of tubes receiving buffer instead of HCG solution is determined. The ratio of this fluorescent signal difference to the total fluorescent signal entrapped in liposomes is a measure of the extent of liposome lysis attributable to the presence of HCG. The maximal total fluorescent signal in each tube is measured after 200 μl of 10% octylglucoside are added to maximally lyse the liposomes. The results are illustrated in Table 4 below.

TABLE 4

| HCG (mIU/ml) | % F(ab')$_2$ Liposome Lysis* | |
|---|---|---|
| | Human Plasma Complement | Rabbit Serum Complement |
| 780 | 61 | 45 |
| 300 | 59 | 45 |
| 10 | 4 | 4 |
| 2 | 0.3 | 0.2 |

*F(ab')$_2$/Liposome = 33 μg/μmole

In this example, a greater than 10,000 fold higher concentration of analyte (as compared to Example 6) is used because of the relatively lower sensitivity observed using anti-HCG F(ab')$_2$ coupled liposomes. Nevertheless, the sensitivity of this example is still one hundred times greater than that obtained for example by Umeda, et al.

The non-specific lysis of antibody-coupled liposomes, mediated by plasma or serum used as a complement source, is in part due to the presence of the Fc portion of whole antibody on liposomes as for example in Umeda, et al. This part of "interference" is eliminated when fragments are used which do not contain the Fc portion of the antibody molecule, i.e., F(ab')$_2$ fragments. In a separate experiment, it was established that the anti-HCG/complement mediated lysis of HCG-coupled liposomes is abolished by the removal of Fc fragments from the anti-HCG antibodies.

One of the goals in developing immunoassay systems is to be able to use complement from any animal source. Example 7 also demonstrates that different animal serum or plasma, i.e., rabbit, human, goat, etc., can be used as a complement source in this particular system using F(ab')$_2$ coupled liposomes whereas only guinea pig serum is an appropriate complement reagent in the particular system of Umeda, et al.

EXAMPLE 8

Immunoassay Using Anti-HCG F(ab')$_2$ and Using Double Antibody Immune Precipitates The double antibody immune precipitate suspension described above in Example 4 is diluted 1000-fold prior to use in the assay. To each of a set of six tubes is added 50 μl of the diluted immune precipitate suspension. To each duplicate set of tubes is added 50 μl of antigen solution containing 100, 10 and 0 mIU/mL HCG. After the reaction mixture is incubated at 37° C. for 30 minutes, 50 μl of F(ab')$_2$-liposomes (80 nmole/ml) is added into each tube and the incubation of tubes is continued at 37° C. for 30 minutes. The lysis of liposomes is initiated by the addition of 150 μl of a freshly prepared 40% human plasma followed by incubating the mixture at 37° C. for 3 minutes. At the end of this period, the reaction is stopped by adding 700 μl of HEPES-gelatin buffer containing 35.7 mM EDTA, and the fluorescent signal in each tube is measured. The results shown in Table 5 below indicate an HCG dose-dependent lysis of liposomes.

TABLE 5

| Fluorescent Intensity | |
|---|---|
| HCG (mIU/ml) | Fluorescent* Signal/Noise |
| 100 | 27 |
| 10 | 12 |
| 0 | 0 |

*Signal Noise = (Fluorescent intensity difference of HCG containing sample and blank control)/(Standard deviation of fluorescent intensity of blank control)

EXAMPLE 9

Immunoassay Using Anti-HCG F(ab')$_2$ and Using Antibody Coated Carboxylated Polystyrene Particles The antibody coated carboxylated polystyrene particles described in Example 5 are diluted to a final concentration of 38 μg/ml (1.4×10$^8$ particles/ml). The assay procedures are the same as those described in Example 8 except that the polystyrene particles are used instead of the double antibody immune precipitates. The results are summarized in Table 6 indicating a HCG dose-dependent lysis of liposomes.

TABLE 6

| Fluorescent Intensity | |
|---|---|
| HCG (mIU/ml) | Fluorescent* Signal/Noise |
| 780 | 47 |
| 500 | 35 |
| 100 | 13 |
| 10 | 3 |
| 0 | 0 |

*Signal Noise = (Fluorescent intensity difference of HCG containing sample and blank control)/(Standard deviation of fluorescent intensity of blank control)

One advantage of the assay system illustrated by Examples 8 and 9 is that liposomes were added during the last step of the assay thereby avoiding (reducing) interaction-time with the antigen-containing sample which is frequently contaminated with materials which interfere with the assay.

The foregoing illustrative examples relate to a homogeneous immunoassay system involving complement-mediated lysis of liposomes containing fluorophore. While the present invention has been described in terms of specific methods and compositions, it is understood that variations and modifications will occur to those skilled in the art upon consideration of the present invention.

For example, inasmuch as liposomes other than those specifically described herein have been successfully used, and are, therefore likely to be similarly effective according to the present invention, it is intended that other liposome preparations (MLV, SUV, REV, etc.) made with other lipids and lipid conjugates and encapsulating other markers (e.g., enzymes, enzyme substrates, cofactors; dyes, haptens, nucleic acid probes, antigens, antibodies, etc.) and the like be included within the scope of the present invention.

Further, while antibody fragments, such as Fab' and F(ab')₂ have been described which are antibodies to the analyte HCG, other antibody fragments to other antigens, not specifically mentioned herein, would be equally as effective and are therefore within the scope of the present invention.

Also, while the preferred complement activators are soluble antibodies, double antibody immune precipitates, and carboxylated polysytrene particles coated with antibodies, other complement activators not specifically mentioned herein would also be equally effective.

In addition, other aqueous insoluble solid supports, other than polystyrene particles, such as paper, nitrocellulose filters, millipore filters and the like are likely to be similarly effective according to the present invention and are included within the scope of the present invention.

Other reversible gelating materials, other than agarose, may also be successfully used to immobilize liposomes during the modification of their surface structure and their storage, such as Agar-agar, Agar (Noble), and gelatin and therefore are within the scope of the present invention.

In addition, other inhibitors of non-specific lysis, other than dummy liposomes, such as polystyrene particles, and polysaccharide particles, such as dextran, Sepharose ™, Biogel ™, and Sephadex ™ may be used.

Inasmuch as methods for preparing Fab' antibody fragments in a manner which retains their affinity for their complementary antigen and which results in antibody sensitized liposomes with greatly improved sensitivity in a LILA have been described, it is understood that other dithiol complexing agents, such as arylarsenite, and $CdCl_2$ may be used to stabilize vicinal dithiols and impede intramolecular disulfide formation and other reductive cleavage agents, other then cysteine-HCl, such as mercaptoethylamine dithiothreitol, and mercaptoethanol, as well as other thiol activating agents, other than 5,5'-dithiobis(2-nitrobenzoic acid), such as 2,2'-dipyridine disulfide, 4,4'-dipyridine disulfide and sulfite/tetrathionate, may be employed to prepare derivatized Fab' antibody fragments other than TNB-Fab'.

Numerous modifications and variations in the invention as described in the above illustrative examples are expected to occur to those skilled in the art and consequently only such limitations as appear in the appended claims should be placed thereon.

Accordingly, it intended in the appended claims to cover all such equivalent variations which come with the scope of the invention as claimed.

What is claimed is:

1. A method for coupling antibody to thiol-containing lipid vesicles which reduces reducing lipid vesicle aggregation during the antibody lipid vesicle conjugation comprising:
    adding said antibody and said thiol-containing lipid vesicles to a composition capable of forming a heat reversible gel,
    cooling said antibody and thiol-containing lipid vesicles in said composition to form a gelate containing antibody-lipid vesicle conjugates,
    alkylating said antibody-lipid vesicle conjugates in said gelate, and
    washing and placing said gelate, containing said antibody-lipid vesicle conjugates, into buffer.

2. A method according to claim 1 wherein said composition capable of forming a heat reversible gel is a member selected from the group consisting of polysaccharide gels and gelatin.

3. A method according to claim 1 wherein said antibody is selected from the group consisting of Fab' antibody fragments and F(ab')₂ antibody fragments.

4. A method according to claim 1 wherein said lipid vesicles contain encapsulated marker.

* * * * *